United States Patent [19]

Bünnig

[11] 4,322,403

[45] Mar. 30, 1982

[54] METHOD FOR THE PREPARATION OF AN IMMUNE GLOBULIN SOLUTION SUITABLE FOR INTRAVENOUS USE

[75] Inventor: Karl Bünnig, Bad Münder, Fed. Rep. of Germany

[73] Assignees: Blutspendedienst der Landesverbände des Deutschen Roten Kreuzes Niedersachsen, Oldenburg; Bremen Gemeinnützige G.m.b.H., Springe, both of Fed. Rep. of Germany

[21] Appl. No.: 189,001

[22] Filed: Sep. 22, 1980

Related U.S. Application Data

[63] Continuation of Ser. No. 67,721, Aug. 20, 1979, abandoned.

[30] Foreign Application Priority Data

Aug. 25, 1978 [DE] Fed. Rep. of Germany ....... 2837168

[51] Int. Cl.³ .................... A61K 39/00; A61K 39/395
[52] U.S. Cl. ................................. 424/85; 260/112 B; 424/101; 424/177
[58] Field of Search ............... 424/85, 101; 260/112 B

[56] References Cited

U.S. PATENT DOCUMENTS 3,607,857  7/1971  Nelson ........................... 260/112 B
4,136,094  1/1979  Condie ........................... 260/112 B

*Primary Examiner*—Blondel Hazel
*Attorney, Agent, or Firm*—Allegretti, Newitt, Witcoff & McAndrews

[57] ABSTRACT

An immune globulin solution suitable for intravenous use is produced by purifying a salt-containing solution of an immune globulin in a number of adsorptive purification steps using an aqueous, humid, amorphous, chemically pure silicic acid of sub-microscopically fine distribution as the adsorption agent. In each step, the adsorption agent is suspended in the solution, the suspension is incubated for 30 to 60 minutes at about 20° C. while being stirred and the adsorption agent is removed. During at least the first purification step the pH of the suspension is at a value of about 6.8±0.05 (20° C.) and during a subsequent purification step the pH of the suspension is at a value of about 6.5±0.05 (20° C.).

5 Claims, No Drawings

METHOD FOR THE PREPARATION OF AN IMMUNE GLOBULIN SOLUTION SUITABLE FOR INTRAVENOUS USE

This is a continuation of application Ser. No. 067,721 filed Aug. 20, 1979 now abandoned.

BACKGROUND OF THE INVENTION

1. Field of the Invention

This invention relates to a method for the preparation of an immune globulin solution suitable for intravenous use.

2. Description of the Prior Art

Immune globulin solutions contain antibodies in the same, or a higher, concentration as the starting product, the animal or human blood. They have been in use for 27 years with greater or lesser success in two versions in passive immune prophylaxy, for agamma-globulinaemias and other antibody deficient states and for infectious illnesses. The one version is an intramuscularly (or subcutaneously) applicable solution with a 160 g/l protein concentration and the other an intravenously applicable solution usually with a protein concentration of 50 g/l.

Both the immune globulin intramuscular (i.m.) preparations and also the immune globulin intraveneous (i.v.) preparations can vary considerably according to the method of production and suffer from the disadvantages that are to be found in their differing compatability and therapeutic effect.

Thus, for example, small volumes of a conventional immune globulin i.m. preparation can produce at the injection location painful irritations, which at higher doses become agony for the patient. Another drawback of these preparations is the fact that about one-third of the injected quantity of antibodies is proteolytically broken down, and can therefore develop no further therapeutic action and the effection portion is transported away from the muscular deposition place only relatively slowly, that is too slowly in the case of acute sickness. Since the immune globulin at present commercially available, when used for i.v. application has been found to lead to serious to life threatening anaphylactoid reactions, it has been subjected by the manufacturers of such preparations, when intended for i.v. use, to special physical and chemical treatment methods.

The immune globulin i.v. preparations developed in this way and at present commercially available exhibit, however, other production-related disadvantages, which can likewise be seen in general incompatability reactions, which increase drastically as the dose increases, and in too low and/or one-sided therapeutic effects. The harmful effects with i.v. application can extend, as secondary reaction, from a reddening of the face through a feeling of anxiety, headache, visual disturbances, nausea, vomiting, high temperature, shivering to circulatory failure with loss of consciousness. If, however, the compatability can be termed good, the corresponding immune globulins i.v. preparations are too weak or too one-sided in the context both of antibacterial and antiviral and antitoxic effect, or their dwell time in the patient organism is too short, that is their half-life is clearly less than 18–22 days, the value for intact antibodies of species IgG (see Barandun et al, Schweiz. med. Wschr. 106 (1976) 533–542). As an evaluation scale for the secondary reactions occurring in vivo, an invitro test has proved successful in addition to the known toxicity and pyrogenity tests in animal experiments and the clinical compatability test. This so-called complement forming reaction test ($=$KBR—Test; e.g., method of G. J. Stein and Van Ngu, J. Immunol., 65 (1950) 17–37) permits quantitative determination of substances in immune globulin preparations, which nonspecifically bind the complement. The assumption is adopted today that an immune globulin i.v. preparation with a Lysehemm value of $>50\%$ where 2 C.H50 units are used (see Kabat and Mayer's Experimental Immunochemistry, 2nd Ed., 4th Printing, Charles C. Thomas Publisher, U.S.A.) in a KBR formula comprising 12.5 g/l immune globulin protein content, will to a high degree of probability exhibit individually the above-listed secondary reactions, while preparations with L.H. values $<50\%$ very drastically limit the risk of dangerous secondary reactions. In the production of immune globulins i.v. preparations, methods have been used which in principle differ from one another; these should make it clear that the new method to be put forward here is distinguished from those already known.

Thus, for example, it is known that in order to produce an immune globulin preparation, the gamma globulin fraction of the serum, obtained in the usual way by ammonium sulphate precipitation or alcohol precipitation, may be treated at a pH value of 1.5 to 5.5 at a temperature between 0° and 50° C. for 2 hours to 2 days with pepsin, for example with 25,000 to 200,000 units of pepsin/100 g of protein to be broken down, with continual monitoring of the anticomplementary effect until the non-specific complement fixation is eliminated; the thus produced gamma globulin is then fractionated by precipitation with neutral salts or is ultrafiltered, separated from low-molecular separation products, sterilely filtered and if necessary freeze-dried (DT-Pat. No. 11 48 037).

The disadvantage of this method is that essentially only broken down protein molecules are obtained and that only a few antibodies remain in native form, so that the antibacterial and antiviral effectiveness is very low. Furthermore, it must be taken into account that on the one hand a complete proteolytic elimination of the non-specific complement binding is practically impossible to carry out since native immune globulins are also always broken down, so that the immunological effectiveness of the preparation is questionable. It is also necessary to inactivate the enzymes (e.g., pepsin or plasmin), since otherwise they will continue their proteolytic action during the storage of the preparation.

Attempts have also been made to use polyethylene glycol for the fractionation of blood plasma and for the precipitation of a purified antibody fraction from highly diluted aqueous solutions, but here the existence of non-specifically complement binding substances has not been verified (Chun et al., Anal. Biochem 19 (1967) 481–497).

It is furthermore known to produce an immune globulin preparation, which essentially is free of anticomplementarily active constituents, from a natural antibody-containing starting material, especially plasma, by fractionation and selective precipitation of the disturbing substances and possibly also precipitation of haepatitis virus or antigen, freeing the immune globulin from undesired proteins, after the actual fractionation of the starting material, separating complement-fixing substances from an aqueous solution so that the immune globulin itself remains in solution and adding at least one dissolving-inhibiting agent, namely a water-soluble salt and/or a linear, chainshaped, non-ionic polymer compound, the latter being used in a concentration, the dissolving-inhibiting action of which is essentially the same as that of 4.7–7 g/100 ml of polyethylene glycol with a molecular mass of between 4000 and 8000 Dalton units, whereby the aqueous solution in the latter case contains at most 4 g/100 ml protein (DT-OS No. 22 34 069).

It is furthermore known to produce an intravenously applicable immune globulin preparation by first treating an aqueous solution of a native immune globulin having a weakly alkaline pH with dithiothreitol in a concentration of less than 0.01 mol/liter and a mol ratio to the protein of 2.5 to 50 in the reaction mixture until about 2 to 4 disulphide bonds per globulin molecule are reduced, whereupon an aqueous solution of this reduced product at weakly alkaline pH is alkalized with at least 1 mol-equivalent, referred to dithiothreitol, of iodine acetamide and then the thus obtained, chemically modified immune globulin is separated from the non-protein-containing reaction products and the excess of reaction partners (DT-OS No. 23 11 333). in spite of numerous further investigations and proposals for obtaining an intraveneously usable immune globulin preparation, the products obtained have not so far proved satisfactory, because they either still possess too high Lysehemm values and/or too short a dwell time in the organism or a too low antibacterial, antiviral and antitoxic action so that a purposeful dosing of the preparation is adversely influenced.

It is an object of the present invention to provide a method of producing an intravenously usable immune globulin which does not suffer from the disadvantages of the known preparations or possesses them only in a medically and clinically tolerable extent and which therefore is distinguished by a no longer detectable or only very slight non-specific complement fixing tendency and, by a good antibacterial, antiviral and antitoxic action, depending upon how intensively and how frequently the proposed method is used in the preparation of a product unit.

The method of the present invention can always be used with success when immune globulin fractions containing unacceptable proportions of proteins having an anticomplementary effect need to have these proteins separated from them.

BRIEF SUMMARY OF THE INVENTION

According to the present invention there is provided a method of producing an immune globulin solution soluble for intravenous use in which a salt-containing solution of an immune globulin is purified in a plurality of adsorptive purification steps in each of which an aqueous, humid, amorphous, chemically pure silicic acid of sub-microscopically fine distribution is suspended in the solution as an adsorption agent, the suspension is incubated for 30 to 60 minutes at about 20° C. whilst being stirred and the adsorption agent is removed and in which during at least the first purification step the pH of the suspension is adjusted to a value of 6.8±0.05 (20° C.) and during a subsequent purification step the pH of the suspension is adjusted to a value of 6.5±0.05 (20° C.).

Preferably, the suspension is stirred for 30 minutes at approximately 20° C.

In the after-purification of gamma globulin which has been obtained by the known Cohn fractionating method, it has been found advantageous if, after a clarifying filtration of the highly concentrated immune globulin solution adjusted to a pH of 7.4 (20° C.), and having a protein content of approximately 130 g/l, at least 4 absorbtive purification steps are carried out and the quantity of silicic acid used is determined according to the following equations:

$$C_{Prot.} : C_{Susp.} = 1:z = C_{Prot}^{[g/dl]} : \frac{m_{SiO2-humid}^{[g]} \cdot 100}{V_{Prot.}[ml]} \quad (1)$$

and $$m_{SiO2-humid}^{[g]} = \frac{z \cdot C_{Prot.}^{[g/dl]} \cdot V_{Prot.}^{[ml]}}{100} \quad (2)$$

$C_{Prot.}$ = Concentration of Protein
$C_{Susp.}$ = Concentration of Suspension
g/dl = Grams per Deciliter
$V_{Prot}[ml]$ = Volume of Protein in Milliliters Preferably, the first and second adsorbtive purification steps are carried out at a pH value of 6.80±0.05 (20° C.) and the third and fourth adsorbtive purification steps at a pH value of 6.50±0.05 (20° C.), whereby in the first and third purification steps the obtained clear raw gamma globulin solution has the "silicic acid humid" quantity corresponding to a concentration ratio of 1:z=1:2 added to it and incubated with stirring, and in the second and fourth steps the same process is repeated with a ratio of 1:z=1:1.

The filtrate of the last adsorbtive purification step is, according to the present invention, diluted to a desired concentration (e.g., 50 g/l, 20° C.) and has added to it, during the course of dilution, 3.0 g/l (20° C.) of gelatine, preferably urea-gelatine polymer (HGP plasma substitution agent, e.g. Haemaccel by the firm Behringwerke, Marburg), is adjusted to a pH value of 7.0±0.1 (20° C.) with NaOH solution and the clear, gelatine-containing immune globulin i.v. solution is sterilely filtered. When the clinically recommended quantities are used, HGP adversely affects the coagulation system only by the diluting effect on the blood, does not affect the blood group diagnosis, and anaphylactic reactions seldom occur.

It should be noticed in this context that the solution is only filtrable when the gelatine contained in it is completely dissolved, which is achieved by brief heating up (approximately 15 minutes at 37° C.); with the HGP, which hardly gels as a function of temperature, this problem does not arise. The gelatine has a positive effect upon the storage stability of the end product.

DESCRIPTION OF THE PREFERRED EMBODIMENT

Lyophilized Cohn-fraction II is dissolved in 0.60 g/l (20° C.) of NaCl solution ($K^{20°}$=1.11 mS.cm$^{-1}$) to 130–150 g/l protein concentration and the pH value is adjusted with NaOH solution to 7.4±0.1 (20° C.) The protein concentration to be adjusted is dependent upon the proportion of anticomplementarily acting constituents in the starting material and the desired concentration to be achieved in the end product; experience has shown that enrichments of too highly diluted purified immune globulin solutions lead to the forming of new anticomplementarily acting products. To improve substantially the suitability for filtering of this cloudly solution it is centrifuged at high speed (e.g., for 45 minutes at 45,000 xg, (20° C.), or for 1.5 hours at 25,000 xg (20°

C.), and is then pressured filtered (using a cellulose nitrate membrane, 0.45 μm+glass fiber prefilter).

The anticomplementarily effective constituents in the solution are adsorptively removed with water-humid silicic acid in four purification steps, that is (1) and (2) at pH=6.80±0.05 (20° C.) and (3) and (4) at pH=6.50±0.05 (20°) sufficiently for a haemolysis inhibition of <50% to be achieved at an immune globulin protein concentration of 12.5 g/l in a complement binding reaction formula.

The quantity of silicic acid used in each step is determined according to equations 1 to 2 previously referred to, and in the first and third steps the concentration ratio is $1:z=1:2$ and in the second and fourth steps the concentration ratio is $1:z=1:1$. In each step, the suspension is incubated for 30 to 60 minutes at 20° C. whilst being stirred and the adsorption agent is then removed.

If the necesssity for a fifth purification step arises as a function of the starting material, then it is better to increase the z value in the second and fourth steps so that concentration ratio is increased above $1:z=1:1$ but does not exceed $1:z=1:2$ rather than to increase the number of purification steps as in this way losses of volume are reduced.

The aqueous, humid, amorphous, chemically pure silicic acid of sub-microscopically fine distribution (e.g. Aerosil 130 by the firm Degussa, Frankfurt a.M.) is produced according to the method as a store for one production unit, by precipitating the sterile, dry commercial product with fresh, sterile apyrogenic Ag.dest. to a suspension and then centrifuging this at high speed (see above); the liquid above the precipitate being rejected.

What is claimed is:

1. In a method for making immune globulin solution suitable for intravenous use, which method includes preparing a raw immune globulin solution by the fractionation of blood plasma, said fractionation including adjusting the blood plasma to a pH of greater than about 6.8, a conductivity of greater than about 11.0 mS cm$^{-1}$ (20° C.), and a protein concentration of less than about 65 g/l, then treating said plasma with silicic acid compounds to separate specific proteins therefrom, the improvement comprising, in combination:
   (a) adjusting the protein concentration of said raw immune globulin solution to about 130 g/l;
   (b) adjusting the conductivity of said raw immune globulin solution to about 1.1 mS cm$^{-1}$ (20° C.);
   (c) adjusting the pH of said raw immune globulin solution to and between about 6.5–6.8; and
   (d) treating said raw immune globulin solution with an aqueous, humid, amorphous, chemically pure silicic acid compound of submicroscopically-fine distribution, followed by separating said immune globulin solution, so treated, from said silicic acid compounds to yield an immune globulin solution suitable for intravenous use.

2. In a method for making immune globulin solution suitable for intravenous use, which method includes preparing a raw immune globulin solution by the fractionation of blood plasma, said fractionation including adjusting the blood plasma to a pH of greater than about 6.8, a conductivity of greater than about 11.0 mS cm$^{-1}$ (20° C.), and a protein concentration of less than about 65 g/l, then treating said plasma with silicic acid compounds to separate specific proteins therefrom, the improvement comprising, in combination:
   (a) adjusting the protein concentration of said raw immune globulin solution to between about 130 and 150 g/l;
   (b) adjusting the conductivity of said raw immune globulin solution to about 1.1 mS cm$^{-1}$ (20° C.);
   (c) adjusting the pH of said raw immune globulin solution to between about 6.5–6.8; and
   (d) treating said raw immune globulin solution with an aqueous, humid, amorphous, chemically pure silicic acid compound of submicroscopically-fine distribution, followed by separating said immune globulin solution, so treated, from said silicic acid compounds to yield an immune globulin solution suitable for intravenous use.

3. In a method for making immune globulin solution suitable for intravenous use, which method includes preparing a raw immune globulin solution by the fractionation of blood plasma, said fractionation including adjusting the blood plasma to a pH of greater than about 6.8, a conductivity of greater than about 11.0 mS cm$^{-1}$ (20° C.), and a protein concentration of less than about 65 g/l, then treating said plasma with silicic acid compounds to separate specific proteins therefrom, the improvement comprising, in combination:
   (a) adjusting the protein concentration of said raw immune globulin solution to between about 130 and 150 g/l;
   (b) admixing a salt-containing solution of an immune globulin with an aqueous, humid, amorphous, chemically pure silicic acid of submicroscopically-fine distribution;
   (c) stirring the mixture for 30 to 60 minutes at about 20° C. while maintaining the pH of the mixture at a pH of 6.8±0.05;
   (d) separating the silicic acid with adsorbed impurities from the immune globulin solution;
   (e) repeating steps (b), (c), and (d) on the treated globulin solution of step (d);
   (f) repeating steps (b), (c), and (d) on the treated globulin solution of step (e), but while maintaining the pH of step (c) at 6.5±0.05; and
   (g) repeating steps (b), (c), and (d) on the treated globulin solution of step (f), but while maintaining the pH of step (c) at 6.5±0.05.

4. A method according to claim 3 in which for the first and third adsorptive purification steps (b) and (f) the quantity of silicic acid suspended in the solution corresponds to a concentration ratio of $1:z=1:2$ and for the second and fourth adsorptive purification steps (e) and (g) the quantity of silicic acid suspended in the solution corresponds to a concentration ratio of $1:z=1:1$.

5. A method according to claim 3 in which the solution remaining after removal of the adsorptive agent in the last adsorptive purification step (g) is diluted and is adjusted during dilution both with: (1) gelatine to a concentration of about 3.0 g/l (20° C.); and (2) NaOH solution to a pH value of about 7.0±0.1 (20° C.), and the clear, colorless, gelatine solution is sterilely filtered.

* * * * *